(12) United States Patent
Dziezok et al.

(10) Patent No.: US 9,259,363 B2
(45) Date of Patent: Feb. 16, 2016

(54) SEALED CORE FOR AN ABSORBENT ARTICLE

(71) Applicant: The Procter & Gamble Company, Cincinnati, OH (US)

(72) Inventors: Peter Dziezok, Hochheim (DE); Ralf Geilich, Eppstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 228 days.

(21) Appl. No.: 13/919,043

(22) Filed: Jun. 17, 2013

(65) Prior Publication Data

US 2013/0310783 A1  Nov. 21, 2013

Related U.S. Application Data

(63) Continuation of application No. 11/329,796, filed on Jan. 11, 2006, now Pat. No. 8,512,305.

(30) Foreign Application Priority Data

Jan. 11, 2005  (EP) .................................... 05000391

(51) Int. Cl.
  *A61F 13/53* (2006.01)
  *A61F 13/539* (2006.01)
  (Continued)

(52) U.S. Cl.
  CPC ......... *A61F 13/539* (2013.01); *A61F 13/15203* (2013.01); *A61F 13/534* (2013.01)

(58) Field of Classification Search
  CPC ......... A61F 13/02; A61F 13/15; A61F 13/47; A61F 13/49; A61F 13/505; A61F 13/511; A61F 13/53; A61F 13/534; A61L 15/16; A61L 15/18; A61L 15/20; A61L 15/42; A61L 15/58; A61L 24/00; C08J 3/12; C08J 5/04; C09J 5/04
  See application file for complete search history.

(56) References Cited

U.S. PATENT DOCUMENTS 3,860,003 A   1/1975  Buell
3,929,135 A  12/1975  Thompson
(Continued)

FOREIGN PATENT DOCUMENTS

DE   10002149   7/2001
EP    0172035   2/1986
(Continued)

OTHER PUBLICATIONS

International Search Report and Written Opinion, PCT/US2006/000648, date of mailing Apr. 26, 2006.
(Continued)

*Primary Examiner* — Melanie Hand
(74) *Attorney, Agent, or Firm* — Christian M. Best

(57) ABSTRACT

An absorbent article is provided including a topsheet, a backsheet, and an absorbent core disposed between the topsheet and the backsheet. The core defines a wearer facing side oriented towards a wearer when the article is being worn and an opposed garment facing side. The core includes a storage layer that also defines a wearer facing side and an opposed garment facing side. The core further includes a first core wrap sheet covering the wearer facing side of the storage layer, and a second core wrap sheet covering the garment facing side of the storage layer. The first core wrap sheet is joined to the second core wrap sheet along at least one stripe of juncture. The stripe of juncture extends in at least one of the transversal and longitudinal directions.

30 Claims, 3 Drawing Sheets

(51) Int. Cl.
 *A61F 13/15* (2006.01)
 *A61F 13/534* (2006.01)

(56) References Cited

U.S. PATENT DOCUMENTS

| | | | |
|---|---|---|---|
| 4,573,986 | A | 3/1986 | Minetola et al. |
| 4,834,735 | A | 5/1989 | Alemany et al. |
| 5,037,416 | A | 8/1991 | Allen et al. |
| 5,102,484 | A | 4/1992 | Allen et al. |
| 5,124,111 | A | 6/1992 | Keller et al. |
| 5,151,092 | A | 9/1992 | Buell et al. |
| 5,269,775 | A | 12/1993 | Freeland et al. |
| 5,458,592 | A | 10/1995 | Abuto et al. |
| 5,462,538 | A | 10/1995 | Korpman |
| 5,569,234 | A | 10/1996 | Buell et al. |
| 5,625,222 | A | 4/1997 | Yoneda et al. |
| 5,885,681 | A | 3/1999 | Korpman |
| 5,980,500 | A | 11/1999 | Shimizu et al. |
| 6,004,306 | A | 12/1999 | Robles et al. |
| 6,437,214 | B1 | 8/2002 | Everett et al. |
| 6,717,028 | B1 | 4/2004 | Oberstadt |
| 8,512,305 | B2 | 8/2013 | Dziezok et al. |
| 2002/0165477 | A1 | 11/2002 | Dunshee |
| 2004/0162536 | A1 | 8/2004 | Becker et al. |
| 2005/0158539 | A1 | 7/2005 | Murphy et al. |
| 2006/0155254 | A1 | 7/2006 | Sanz et al. |

FOREIGN PATENT DOCUMENTS

| | | |
|---|---|---|
| EP | 0570016 | 11/1993 |
| EP | 0847263 A1 | 6/1998 |
| EP | 1088537 A2 | 4/2001 |
| EP | 0847263 B1 | 1/2002 |
| EP | 0926287 B1 | 10/2003 |
| EP | 1447066 | 10/2008 |
| JP | 2001-161748 | 6/2001 |
| JP | 2002-113800 | 4/2002 |
| JP | 2003-165173 | 6/2003 |
| WO | WO 95/11654 | 5/1995 |
| WO | WO 00/00230 | 1/2000 |
| WO | WO 0064396 A1 | 11/2000 |

OTHER PUBLICATIONS

All Office Actions, U.S. Appl. No. 11/329,796.
Whitmore, Darryl L., "Nonwovens Containing Immobilized Superabsorbent Polymer Particles", INJ, vol. Fall, 2003.

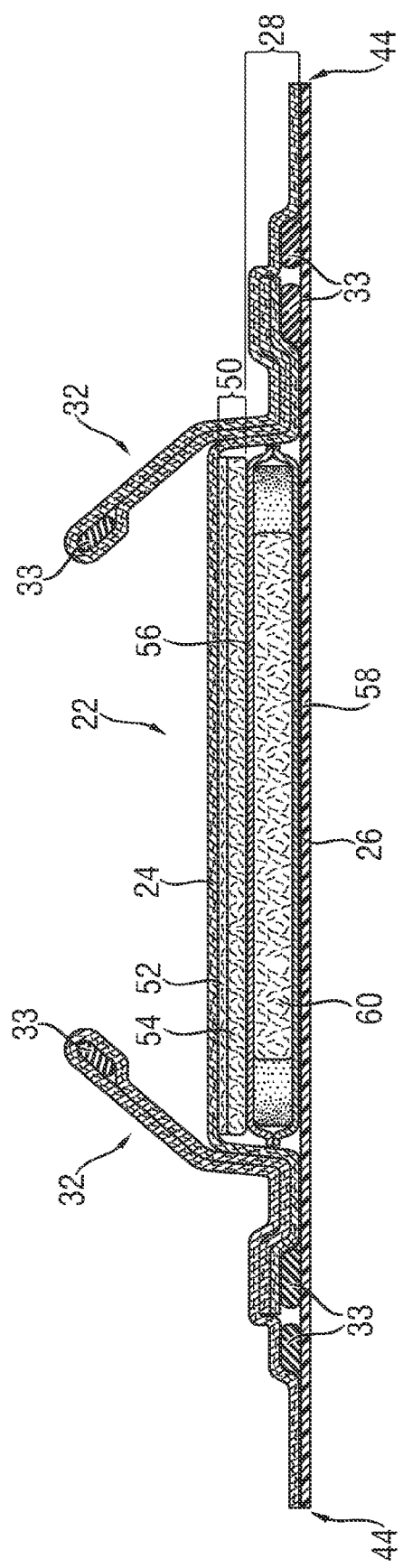

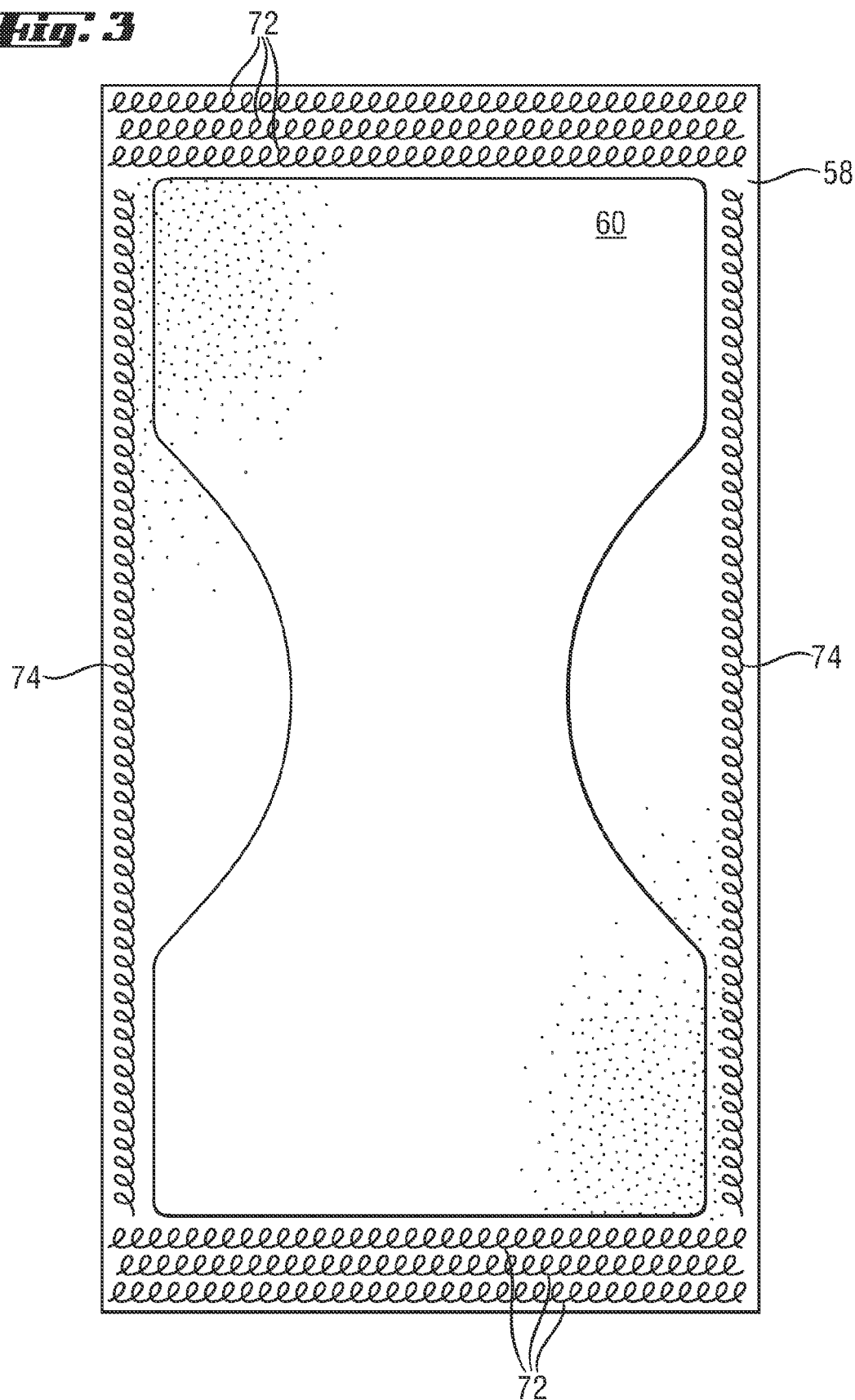

SEALED CORE FOR AN ABSORBENT ARTICLE

CROSS REFERENCE TO RELATED APPLICATIONS

This application claims priority under 35 U.S.C. §120 to, and is a continuation of, U.S. patent application Ser. No. 11/329,796, filed on Jan. 11, 2006, which claims priority under 35 U.S.C. §119 to European Patent Application No. 05000391.2, filed on Jan. 11, 2005, the entire disclosures of which are incorporated herein by reference.

FIELD

The present invention relates to absorbent articles, such as diapers and sanitary napkins, and cores useful for such articles. More specifically, the present invention relates to absorbent cores for such articles and the enveloping of such cores.

BACKGROUND

Disposable absorbent articles are broadly available and consumers are used to a high performance for the collecting and retaining of menses (in the case of sanitary napkins or panty liners) or for the collecting and retaining urine and fecal material (in the case of e.g. disposable diapers). From such articles consumers expect a superior absorbency behavior and at the same time expect excellent the wearing comfort and the dryness when being worn.

Often, such articles comprise multiple absorbent members, at least one member being primarily designed to store liquid, and at least one other member primarily designed to acquire and/or distribute liquid, the members typically being encapsulated between a topsheet (on the wearer facing side) and a backsheet (on the garment facing side).

In modern absorbent articles the absorbent core will typically comprise a superabsorbent material in combination with a fibrous material, for example cellulose. In particular, the storage layer will be provided from a combination of such materials. It is important to maintain the integrity of such absorbent core, both when the article is dry and when the article is wet, that means before use and in use. It is also important to prevent the escape of any of the absorbent materials providing the core, in particular the escape of super-absorbent materials, which are often provided in the form of particles. The escape of super-absorbent materials from the core could ultimately lead to contact of such superabsorbent materials with the skin of the wearer. This phenomenon is known as gel on skin (as the super-absorbent materials are often also referred to as hydrogels). However, such gel on skin occurrences are considered undesirable as many consumers consider the skin contact of such super-absorbent material to be unpleasant. Some recent absorbent articles, especially disposable diapers, employ relatively open topsheet structures. These open topsheets promote the absorbance or at least the adherence of high viscosity exudates, such as bowel movement. However, when it's specifically comes to gel on skin problems, these open topsheet structures present a challenge, as they do not represent a highly effected barrier for super-absorbent particles, which may escape from the absorbent core of the absorbent article.

U.S. Pat. No. 4,573,986 (filed in 1984) discloses an early attempt for obviating lifting out of fibers and particulate matters from the absorbent core of an absorbent garment. A wet-strength-tissue envelope is disclosed in which the absorbent core is disposed and secured. The wet-strength-tissue paper or a similar laminate is secured in face to face relation with the core by an open pattern of adhesive, which may, for example, comprise a fine pattern of globulettes of adhesive. Alternatively, a reticulated network of filaments of adhesives can be used.

EP 847 263 (filed in 1995) discloses a more recent core wrap material: Disclosed is a core wrap made from a fibrous non-woven web, preferably a polypropylene meltblown non-woven material. This core wrap material may be folded over on itself and then sealed using, for example, adhesives, heat and/or pressure. In this context, ultrasonic bonder, thermo-mechanically bonding means and adhesives are specifically disclosed as suitable sealing means.

EP 1 088 537 (filed in 2000) discloses a highly water absorbent sheet. This absorbent sheet comprises fine cellulose fibers which provide a fibrous network holding solid super-absorbent particles in position. In order to prevent the escaping of such superabsorbent particles, the disclosed absorbent sheet relies on a hot-melt adhesive forming a further fibrous network and covering the super-absorbent particles.

WO 00/64396 (filed in 2000) discloses yet a further approach for integrity and immobilization enhancement for an absorbent member. The method comprises the application of a foamable movement obstruction agent to an absorbent member.

As to provide the desired absorbency to the article, at least the storage member will typically comprise super-absorbent material, which is admixed with the traditionally used pulp fiber material. Such super-absorbent materials can absorb many times (e.g. 10, or 30 times) their own weight and are therefore very helpful when designing an article of improved fluid handling properties. Many recent products employ higher and higher concentrations of super-absorbent materials, that is concentrations in excess of 50% of the total weight of the storage member. These products achieve a high absorbing capacity with a very thin storage member and are thereby typically overall thin products. While super-absorbent materials can store very large amounts of liquid, they are often not able to distribute the liquid from the point of impact to more remote areas of the absorbent article and to acquire the liquid as fast as it may be received by the article.

Hence, the prior art has disclosed various attempts to prevent the escaping of super-absorbent particles from the absorbent core. However, especially when it comes to absorbent cores with high concentrations of super-absorbent material and the use of relatively open topsheet structures, an even more efficient prevention of the escaping of super-absorbent particles from the absorbent core is desirable.

SUMMARY

In accordance with one aspect of the present disclosure, an absorbent article is provided that extends along a longitudinal axis and a transverse axis. The absorbent article includes a topsheet, a backsheet, and an absorbent core disposed between the topsheet and the backsheet. The core defines a wearer facing side oriented towards a wearer when the article is being worn and an opposed garment facing side. The core includes 1) a storage layer defining a wearer facing side and an opposed garment facing side, 2) a first core wrap sheet covering the wearer facing side of the storage layer, and 3) a second core wrap sheet covering the garment facing side of the storage layer, wherein the first core wrap sheet is joined to the second core wrap sheet along at least one stripe of juncture. The stripe of juncture extends in at least one of the longitudinal and transversal directions.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

FIG. 2 is a cross-sectional view of the disposable diaper shown in FIG. 1; and

FIG. 3 is a top plan view of the storage layer comprised by the absorbent core of a disposable diaper as shown in FIG. 1.

DETAILED DESCRIPTION

Definitions

Figure 1:
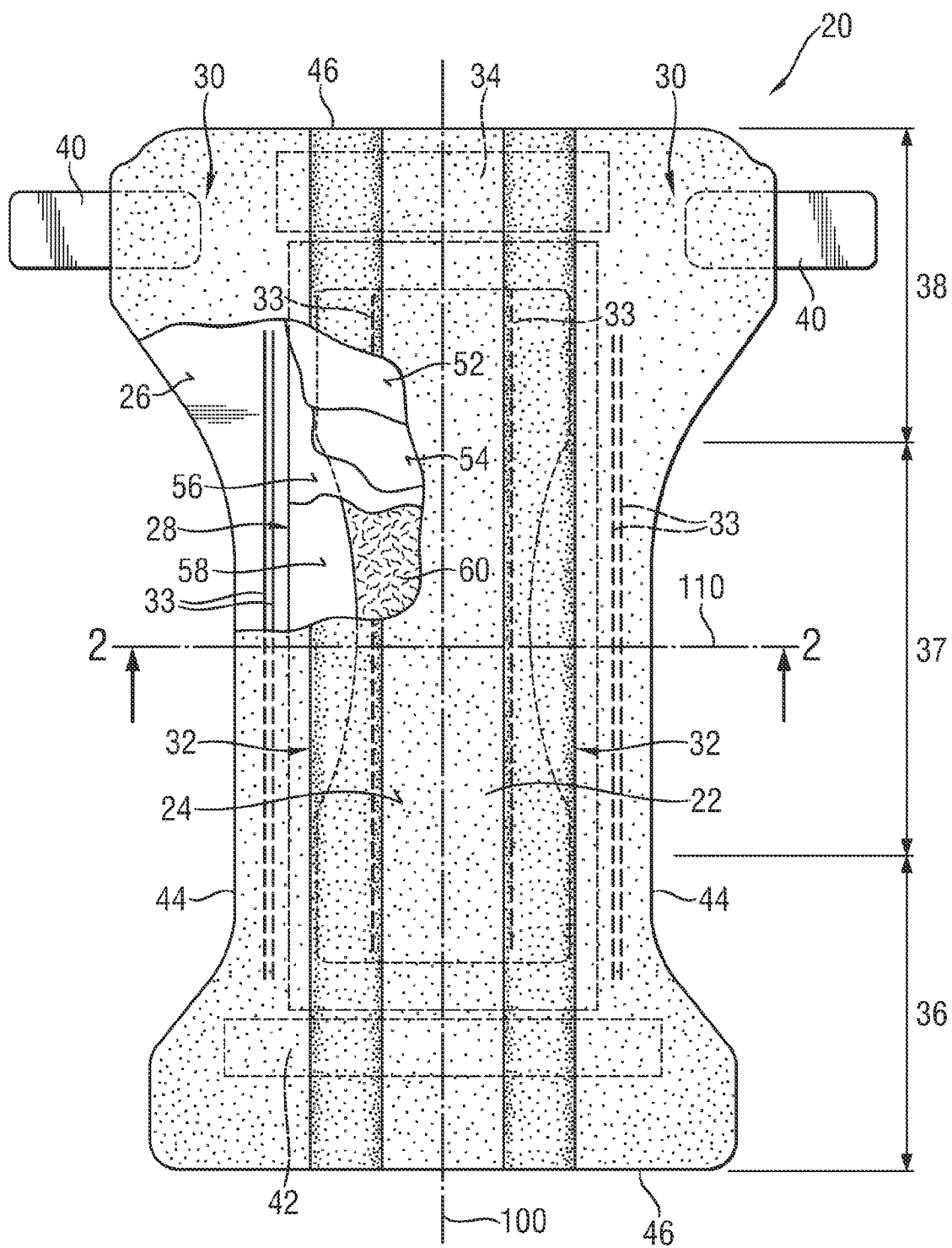
FIG. 1 is a top plan view of a disposable diaper, with the upper layers partially cut away.

As used herein, the following terms have the following meanings:

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinent briefs, training pants, diaper holders and liners, sanitary napkins and the like. Absorbent articles also include wipes, such as household cleaning wipes, baby wipes, and the like.

"Disposable" is used herein to describe articles that are generally not intended to be laundered or otherwise restored or reused i.e., they are intended to be discarded after a single use and, preferably, to be recycled, composted or otherwise disposed of in an environmentally compatible manner.

"Disposed" is used to mean that an element(s) is formed (joined and positioned) in a particular place or position as a unitary structure with other elements or as a separate element joined to another element.

"Diaper" refers to an absorbent article generally worn by infants and incontinent persons about the lower torso.

The terms "thickness" and "caliper" are used herein interchangeably.

"Attached" or "Joined" encompasses configurations whereby an element is directly secured to another element by affixing the element directly to the other element, and configurations whereby an element is indirectly secured to another element by affixing the element to intermediate member(s) which in turn are affixed to the other element.

"Comprise," "comprising," and "comprises" is an open ended term that specifies the presence of what follows e.g. a component but does not preclude the presents of other features, elements, steps or components known in the art, or disclosed herein.

The term "hydrophilic" describes fibers or surfaces of fibers, which are wettable by aqueous fluids (e.g. aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

The terms "fiber" and "filament" are used interchangeably.

The terms "nonwoven", "nonwoven fabric" and "nonwoven web" are used interchangeable.

The disposable article 20 has two centerlines, a longitudinal centerline 100 and a transverse centerline 110.

The term "longitudinal", as used herein, refers to a line, axis or direction in the plane of the disposable article 20 that is generally aligned with (e.g., approximately parallel to) a vertical plane which bisects a standing wearer into left and right body halves when the disposable article 20 is worn.

The terms "transverse" or "lateral" as used herein, are interchangeable, and refer to a line, axis or direction which lies in the plane of the disposable article 20 that is generally perpendicular to the longitudinal direction.

Absorbent Articles

FIG. 1 is a plan view of a diaper 20 as a preferred embodiment of an absorbent article according to the present invention. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20. The chassis 22 comprises an outer covering including a liquid pervious topsheet 24 and/or a liquid impervious backsheet 26. The chassis may also include most or all of the absorbent core 28 encased between the topsheet 24 and the backsheet 26. The chassis preferably further includes side panels 30, leg cuffs 32 and a waist feature 34. The leg cuffs and the waist feature typically comprise elastic members 33. One end portion of the diaper 20 is configured as the front waist region 36 of the diaper 20. The opposite end portion is configured as the rear waist region 38 of the diaper 20. An intermediate portion of the diaper 20 is configured as the crotch region 37, which extends longitudinally between the front and rear waist regions 36 and 38. The crotch region 37 is that portion of the diaper 20 which, when the diaper 20 is worn, is generally positioned between the wearer's legs. The waist regions 36 and 38 may include a fastening system comprising fastening members 40 preferably attached to the rear waist region 38 and a landing zone 42 attached to the front waist region 36. The diaper 20 has a longitudinal axis and centerline 100 and a transverse axis and centerline 110. The periphery of the diaper 20 is defined by the outer edges of the diaper 20 in which the longitudinal edges 44 run generally parallel to the longitudinal axis 100 of the diaper 20 and the end edges 46 run generally parallel to the transverse axis 110 of the diaper 20.

For unitary absorbent articles, the chassis 22 comprises the main structure of the diaper with other features added to form the composite diaper structure. While the topsheet 24, the backsheet 26, and the absorbent core 28 may be assembled in a variety of well-known configurations, preferred diaper configurations are described generally in U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 24 in FIG. 1 may be fully or partially elasticized or may be foreshortened to provide a void space between the topsheet 24 and the absorbent core 28. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 26 in FIG. 1 is generally the portion of the diaper 20 positioned with the absorbent core 28 between the backsheet 26 and the topsheet 24. The backsheet 26 may be joined with the topsheet 24. The backsheet 26 prevents the exudates absorbed by the absorbent core 28 and contained within the article 20 from soiling other external articles that may contact the diaper 20, such as bed sheets and undergarments. In preferred embodiments, the backsheet 26 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE.

The absorbent core 28 in FIG. 1 generally is disposed between the topsheet 24 and the backsheet 26. The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers, absorbent gelling materials, or any other known absorbent material or combinations of materials. The absorbent core may further comprise minor amounts (typically less than 10%) of non-liquid absorbent materials, such as adhesives, waxes, oils and the like.

Exemplary absorbent structures for use as the absorbent assemblies are described in U.S. Pat. No. 4,834,735, entitled "High Density Absorbent Members Having Lower Density and Lower Basis Weight Acquisition Zones", issued to Alemany et al. on May 30, 1989; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997.

The diaper 20 may also include such other features as are known in the art including front and rear ear panels, waist cap features, elastics and the like to provide better fit, containment and aesthetic characteristics. Such additional features are well known in the art and are described in U.S. Pat. No. 3,860,003 entitled "Contractable side portions for disposable diaper" issued to Buell et al. on Jan. 14, 1975 and U.S. Pat. No. 5,151,092 entitled "Absorbent article with dynamic elastic waist feature having a predisposed resilient flexural hinge" issued to Buell et al. on Sep. 29, 1992.

In order to keep the diaper 20 in place about the wearer, the waist regions 36 and 38 may include a fastening system comprising fastening members 40 preferably attached to the rear waist region 38. In a preferred embodiment the fastening system further comprises a landing zone 42 attached to the front waist region 36. The fastening member is attached to the front waist region 36, preferably to the landing zone 42 to form leg openings and an article waist.

Diapers 20 according to the present invention may be provided with a re-closable fastening system or may alternatively be provided in the form of pant-type diapers.

The fastening system and any component thereof may include any material suitable for such a use, including but not limited to plastics, films, foams, nonwoven webs, woven webs, paper, laminates, fiber reinforced plastics and the like, or combinations thereof. It may be preferable that the materials making up the fastening device be flexible. The flexibility is designed to allow the fastening system to conform to the shape of the body and thus, reduces the likelihood that the fastening system will irritate or injure the wearer's skin.

FIG. 2 shows a cross-sectional view of FIG. 1 taken in the transverse axis 110. Starting from the wearer facing side the diaper comprises the topsheet 24, the components of the absorbent core 28, and the backsheet 26. The absorbent core preferably comprises an acquisition system 50, which comprises an upper acquisition layer 52 facing towards the wearer and a lower acquisition layer 54. In one preferred embodiment the upper acquisition layer comprises a nonwoven fabric whereas the lower acquisition layer preferably comprises a mixture of chemically stiffened, twisted and curled fibers, high surface area fibers and thermoplastic binding fibers. In another preferred embodiment both acquisition layers are provided from a non-woven material, which is preferably hydrophilic. The acquisition layer preferably is in direct contact with the storage layer 60.

The storage layer 60 is preferably wrapped by a core wrap material. In one preferred embodiment the core wrap material comprises a first core wrap layer 56 (top layer) and a second core wrap layer 58 (bottom layer). The first core wrap layer 56 and the second core wrap layer 58 can be provided from a non-woven material. One preferred material is a so-called SMS material, comprising a spunbonded, a melt-blown and a further spunbonded layer. The first core wrap layer 56 and the second core wrap layer 58 may be provided from two or more separate sheets of materials or they may be alternatively provided from a unitary sheet of material. Such a unitary sheet of material may be wrapped around the storage layer 60, e.g. in a C-fold. The first core wrap layer 56 and the second core wrap layer 58 may also be joined to each other, preferably along their periphery. In one preferred option both layers are joined along their longitudinal peripheries, in other embodiments they are joined along the transversal peripheries, or along the longitudinal and the transversal peripheries. The joining can be achieved my multiple means well known in the art, eg. by adhesive means, using a continuous or a discontinuous pattern, and preferably a linear or curvilinear pattern.

The storage layer 60 typically comprises fibrous materials, mixed with superabsorbent, absorbent gelling materials. Other materials described above as suitable for the absorbent core 28 may also be comprised. Preferred storage layer according to the present invention may comprise a superabsorbent material in an amount corresponding to at least 30%, or at least 40%, or at least 50%, or at least 60%, or at least 70%, or at least 80% or at least 90% of the total weight of the storage layer.

A upper liquid acquisition layer 52 useful in a diaper according to the present invention may comprise any of the nonwoven fabrics described below. A preferred liquid acquisition layer 52 comprises a binder comprising a styrene-butadiene latex binder. Preferably, the styrene-butadiene latex binder has a carboxylation level of at least 10%, preferably at least 12%. Preferably, the upper liquid acquisition layer 52 comprises polyester fibers and the liquid acquisition layer comprises 20 to 40 weight percent of styrene-butadiene latex binder, and 60 to 80 weight percent of said polyester fibers. Even more preferably, the polyester fibers comprise 20 to 80 weight percent of a first type of fibers, and 20 to 80 weight percent of a second type of fibers, the second type of fibers comprising spiral-crimp fibers. Highly preferred are upper liquid acquisition layers wherein the first type of fibers exhibits a flat crimp and wherein the second type of fibers comprises hollow chemically homogeneous bi-component fibers. Also highly preferred are any upper liquid acquisition layers wherein the polyester fibers are carded to form a nonwoven.

Preferred acquisition systems may also comprise superabsorbent materials. Such acquisition systems may also comprise a single acquisition layer or multiple acquisition layers. Where multiple acquisition layers are comprised any of these layer may comprise superabsorbent materials. Such superabsorbent material may be comprised in an amount corresponding to at least 30%, or at least 50% or at least 70%, at times even in an amount of 100% of the total weight of the respective acquisition layer.

Nonwoven Fabrics

A nonwoven fabric is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled.

The fibres may be of natural or man-made origin. They may be staple or continuous filaments or be formed in situ.

Nonwoven fabrics can be formed by many processes such as meltblowing, spunbonding, carding. The basis weight of nonwoven fabrics is usually expressed in grams per square meter (gsm).

Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Fibers are classified according to their origin, chemical structure, or both. They can be braided into ropes and cordage, made into felts (also called nonwovens or nonwoven fabrics), woven or knitted into textile fabrics, or, in the case of high-strength fibers, used as reinforcements in composites—that is, products made of two or more different materials.

The nonwoven fabrics may comprise fibers made by nature (natural fibers), made by man (synthetic or man-made), or combinations thereof. Example natural fibers include but are not limited to: animal fibers such as wool, silk, fur, and hair; vegetable fibers such as cellulose, cotton, flax, linen, and hemp; and certain naturally occurring mineral fibers. Synthetic fibers can be derived from natural fibers or not. Example synthetic fibers, which are derived from natural fibers include but are not limited to rayon and lyocell, both of which are derived from cellulose, a natural polysaccharide fiber. Synthetic fibers, which are not derived from natural fibers can be derived from other natural sources or from mineral sources. Example synthetic fibers not derived from natural sources include but are not limited to polysaccharides such as starch. Example fibers from mineral sources include but are not limited to polyolefin fibers such as polypropylene, polyethylene fibers and polyester, which are derived from petroleum, and silicate fibers such as glass and asbestos.

Nonwoven webs can be formed by direct extrusion processes during which the fibers and webs are formed at about the same point in time, or by preformed fibers, which can be laid into webs at a distinctly subsequent point in time. Example direct extrusion processes include but are not limited to: spunbonding, meltblowing, solvent spinning, electrospinning, and combinations thereof typically forming layers.

Example "laying" processes include wetlaying and drylaying. Example drylaying processes include but are not limited to airlaying, carding, and combinations thereof typically forming layers. Combinations of the above processes yield nonwovens commonly called hybrids or composites. Example combinations include but are not limited to spunbond-meltblown-spunbond (SMS), spunbond-carded (SC), spunbond-airlaid (SA), meltblown-airlaid (MA), and combinations thereof, typically in layers. Combinations which include direct extrusion can be combined at about the same point in time as the direct extrusion process (e.g., spinform and coform for SA and MA), or at a subsequent point in time. In the above examples, one or more individual layers can be created by each process. For instance, SMS can mean a three layer, 'sms' web, a five layer 'ssmms' web, or any reasonable variation thereof wherein the lower case letters designate individual layers and the upper case letters designate the compilation of similar, adjacent layers.

The fibers in a nonwoven web are typically joined to one or more adjacent fibers at some of the overlapping junctions. This includes joining fibers within each layer and joining fibers between layers when there is more than one layer. Fibers can be joined by mechanical entanglement, by chemical bond or by combinations thereof. Fibers can also be joined by heat-bonding, which comprises techniques such as through-air bonding and thermobonding by use of heated calendar rolls.

Preferred Topsheets

Preferred topsheets for use with the present invention are compliant, soft feeling, and non-irritating to the wearer's skin. Further, the topsheet 24 should be liquid pervious, permitting liquids (e.g., urine) to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids contained in the absorbent core 28. Alternatively, the topsheet 24 may be surfactant treated to make it hydrophilic.

The topsheet 24 preferably has a plurality of apertures with an effective aperture size of at least 0.2 square millimeters, more preferably, the plurality of apertures have an effective aperture size of at least 0.5 square millimeters, even more preferably, the plurality of apertures have an effective aperture size of at least 1.0 square millimeters, and most preferably, the plurality of apertures have an effective aperture size of at least 2.0 square millimeters. Effective apertures are those which have a gray level of 18 or less on a standard gray level scale of 0-255, under the image acquisition parameters described in EP 1 032 336 B1. An aperture having a material free area of x square millimeters is to be understood as having an effective aperture size of at least x square millimeters.

The topsheet 24 preferably has an effective open area of at least 15 percent, more preferably the topsheet has an effective open area of at least 20 percent, even more preferably, the topsheet has an effective open area of at least 25 percent, and most preferably the topsheet has an effective open area of at least 30 percent. Preferably, at least 50% or at least 75% of the topsheet surface are provided with such apertures.

Preferred Absorbent Cores

All of the above described fibers and manufacturing techniques can be useful for providing core wrap sheets according to the present invention.

Preferred core wrap sheets are made of a hydrophilic material to promote rapid transfer of liquids (e.g. urine) through at least the first core wrap sheet. If such core wrap sheets are made of a hydrophobic material, such material can be treated to be hydrophilic, for example by treatment with a surfactant.

There are multiple ways to envelope an absorbent core using a first core wrap sheet and a second core wrap sheet, all of which are within the scope of the present invention. For example, two separate wrap sheets may be used, the first core wrap sheet covering the wearer facing side of the core and the second core wrap sheet covering the garment facing sided of the core. Both wrap sheets can then be joined along longitudinally extending stripes of juncture, one stripe of juncture to each side of the absorbent core. Alternatively, the first core wrap sheet can be integral with the second core wrap sheet and be provided from one and the same sheet of material. Then, only one longitudinally extending stripe of juncture needs to be employed as to achieve the enveloping. Such stripe of juncture can either be of the wearer facing side of the core, or on the garment facing side of the core on either lateral side of the core. The overlapping ends of the wrap sheet material, which are to be joined by said stripe of juncture, can be arranged as to create a butt seal or can be arranged as to create an overlapping seal. Both an overlapping seal and a butt seal can be joined using a stripe of juncture in accordance to the present invention.

Referring to FIG. 3, the core wrap sheets may be joined by a longitudinally extending stripe of juncture 74 (for example a side seal) and/or by a transversally extending stripe of juncture 72, which is typically positioned either at the front end of the absorbent core or at the rear end of the absorbent core or at both ends of the absorbent core. Such a transversally extending stripe of juncture can be provided by the same means as a longitudinally extending stripe of juncture.

The stripe of juncture may comprise different elements having a bonding function, herein referred as bonding elements. For example, bonding elements can be provided by adhesive bonding, by thermo-mechanical bonding, by ultrasonic bonding and the like. According to the present invention at least some bonding elements comprise a microfiber adhesive. The area of a rectangle comprising all bonding elements comprising a microfiber adhesive of the stripe of juncture is herein referred to as the total area of the stripe of juncture. According to the present invention, however, the stripe of juncture also comprises an open area. Open area, as used herein, denotes an area where no bonding elements are present.

According to the present invention, the microfiber adhesive preferably comprises microfibers having a diameter of 10 micrometer to 300 micrometer, preferably 20 micrometer to 50 micrometer. A stripe of juncture comprising microfibers can be created by meltblown spraying, spiral spraying, or omega spraying.

Generally, in accordance with the present invention, stripes of juncture having an open area of at least 20%, or at least 30%, or at least 40%, or at least 50%, or at least 60%, or at least 70%, or at least 80%, or at least 90% of their total area are preferred. However, the open area should not be more than 95% of the total area as to ensure reliable bonding.

Core wrap sheets according to the present invention are preferably provided in the form of non-woven webs. More preferably, they are provided from polyolefin, more preferably from polypropylene. Preferred core wrap sheets have a basis weight from 3 gram per $m^2$ to 50 gram per $m^2$, more preferably from 5 gram per $m^2$ to 30 gram per $m^2$, preferably from 8 gram per $m^2$ to 15 gram $m^2$.

The stripe of juncture will provide a certain bond strength between the core wrap sheets. The stripe of junction will have its largest extension in a first direction. The bond strength between the core wrap sheets, as used herein, is to be understood as the tensile strength in a second direction which is perpendicular to the first direction and within the plane defined by the core wrap sheets. To test tensile strength a test specimen of 2.54 cm (1 inch) width is cut at a representative (typically central) position by two cutting lines oriented in the second direction. Tensile strength is then measured using this test specimen of material in accordance with ASTM method D 1876-01, which is modified as follows: The specimen length is 60 mm and unbonded ends of 10 mm length are used for clamping in the grips of the testing machine (see paragraph 5.2 of D 1876-01). The portions of the first and second core wrap sheet forming part of the specimen are used as flexible adherends (see paragraph 5.1 of D 1876-01). Further, tensile strength is reported (in units of Newton divided by centimeter specimen width; N/cm) as the maximum value of the obtained autographic curve (see paragraph 8.1 of D 1876-01).

According to the present invention the stripe of juncture provides preferably a bond strength of at least 0.5 N/cm between the first core wrap sheet (56) and a second core wrap sheet (58). According to the present invention in particular a stripe of juncture oriented in the transversal direction should will this bond strength. Preferably the stripe of juncture provides a bond strength of at least 1.0 N/cm or 1.5 N/cm or 2 N/cm or 3 N/cm.

Without wishing to be bound by theory, it seems particularly beneficial to have stripes of juncture which comprise microfibers and which preferably comprise a large open area. It appears that the occurrence of the gel-on-skin phenomenon is in part caused by super-absorbent particles which in the process of manufacturing are captured within such a line of junction. When a stripe of juncture is provided by continuous adhesive application, the superabsorbent material is limited in its ability to swell by being confined by the adhesive providing the stripe of juncture. However, the super-absorbent particle is likely to swell once the article is in use and receives liquid. When this swelling is highly restricted by the presence of adhesive, the swelling forces are typically high enough to allow swelling in the direction of the core wrap sheets. These core wrap sheets are typically provided by non-woven materials or tissue materials or similar materials which are relatively week. Hence, wherever the stripe of juncture itself does not provide sufficient open or yielding space to accommodate the swelling of super-absorbent particles, such particles will expand in the direction of the core wrap sheets. Therefore, they are likely to escape through the core wrap sheets, often also causing damage to the core wrap sheets. This escaping of super-absorbent material from the core and especially out of the areas of the stripes of juncture appears to noticeably contribute to occurrences of gel-onskin. If, however, in accordance with the present invention a stripe of juncture comprising microfibers is applied, these microfibers present only little resistance to swelling for the superabsorbent particles. In one aspect, individual microfibers may yield to expanding superabsorbent particles as they are relatively elastic, in a further aspect individual fibers may yield to expanding superabsorbent particles as they are relatively weak and break easily, and in a yet further aspect there will often be enough free space between neighboring microfibers which provides room for swelling. Hence, the adhesive will either find a sufficient open area within the stripe of juncture to allow for swelling without exerting any pressure against the wrap sheets and against surrounding adhesive material or the overall surrounding adhesive material will be elastic enough as to allow for swelling within the stripes of juncture while no or very little pressure is exerted towards the core wrap sheets.

In view of these considerations it seems best to select the dimension of the bonding elements and of the areas free of bonding elements in view of the size of the superabsorbent particles which could escape from the absorbent core (28). The value to be considered specifically is the mean diameter of the super-absorbent particles.

The mean diameter is to be determined using EDANA method 420.2-02 entitled "Particle size distribution". This EDANA method is a sieving method and reports the mass fraction in percent for each particle size fraction remaining on the different sieves employed. Based on this report the mean diameter is calculated according to ASTM test method D 1921-96, namely paragraph 13 thereof entitled "Analysis of Particle Distribution".

The spaces free of bonding elements will have a smallest dimension (that is the smallest free width in any direction). According to the present invention this smallest dimension preferably is at least 0.5 times said mean diameter (herein "MD"). More preferably, the smallest dimension is from 0.5 to 3 times the MD, more preferably from 0.5 to 2 times the MD, most preferably from 0.8 to 1.2 times the MD.

Hence, the stripes of juncture according to the present invention provide a sufficient bond strength on a macro level (when looking at the performance of the overall absorbent article), but at the same time sufficient weakness and swelling space on a micro level (when looking at the environment of single particles of super-absorbent material).

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal axis and a transverse axis, the absorbent article comprising: a topsheet; a backsheet; and an absorbent core disposed between the topsheet and the backsheet, the absorbent core defining a wearer facing side oriented towards a wearer when the absorbent article is being worn and an opposed garment facing side, wherein the core comprises 1) a storage layer comprising a wearer facing side and an opposed garment facing side, 2) a first core wrap sheet covering the wearer facing side of the storage layer, and 3) a second core wrap sheet covering the garment facing side of the storage layer, wherein the first core wrap sheet is joined to the second core wrap sheet along a first stripe of juncture, wherein the first stripe of juncture primarily extends in a longitudinal direction, wherein the first core wrap sheet is joined to the second core wrap sheet along a second stripe of juncture, wherein the second stripe of juncture extends primarily in a transversal direction, and wherein the first strip of juncture or the second strip of juncture is non linear.

2. The absorbent article of claim 1, wherein the first stripe of juncture or the second stripe of juncture comprises an adhesive.

3. The absorbent article of claim 1, wherein the first stripe of juncture or the second stripe of juncture comprises a microfiber adhesive.

4. The absorbent article of claim 1, wherein the first stripe of juncture or the second stripe of juncture comprises an open area from about 30% to about 95% of the total area.

5. The absorbent article of claim 1, wherein the absorbent core comprises superabsorbent particles.

6. The absorbent article of claim 1, wherein the first core wrap sheet or the second core wrap sheet has a basis weight from about 3 gram per m$^2$ to about 50 gram per m$^2$.

7. The absorbent article of claim 1, wherein the topsheet comprises a plurality of pores having an effective aperture size of at least 2.0 square millimeters.

8. The absorbent article of claim 1, wherein the storage layer comprises a superabsorbent material, and wherein the superabsorbent material comprises at least 30% of the total weight of the storage layer.

9. The absorbent article of claim 1, wherein the storage layer comprises a superabsorbent material, and wherein the superabsorbent material comprises at least 80% of the total weight of the storage layer.

10. The absorbent article of claim 1, wherein first the stripe of juncture or the second stripe of juncture is continuous.

11. The absorbent article of claim 1, wherein the first stripe of juncture or the second stripe of juncture is discontinuous.

12. The absorbent article of claim 1, wherein the first and second core wrap sheets together surround at least a portion of the storage layer.

13. The absorbent article of claim 1, wherein the first and second core wrap sheets together enclose at least a portion of the storage layer.

14. The absorbent article of claim 1, comprising an acquisition system positioned at least partially intermediate the topsheet and the absorbent core.

15. The absorbent article of claim 1, comprising:
  a third stripe of juncture joining the first core wrap sheet and the second core wrap sheet and that generally extends in at least one of the longitudinal and transversal directions.

16. The absorbent article of claim 1, wherein the first stripe of juncture or the second stripe of juncture is provided by continuous adhesive application.

17. The absorbent article of claim 1, wherein the first stripe of juncture or the second stripe of juncture comprises bonding elements.

18. An absorbent article having a longitudinal axis and a transverse axis, the absorbent article comprising:
  a topsheet;
  a backsheet; and
  an absorbent core disposed between the topsheet and the backsheet, the absorbent core defining a wearer facing side oriented towards a wearer when the absorbent article is being worn and an opposed garment facing side, wherein the core comprises: 1) a storage layer comprising a wearer facing side and an opposed garment facing side, 2) a first core wrap sheet covering the wearer facing side of the storage layer, and 3) a second core wrap sheet covering the garment facing side of the storage layer, wherein the first core wrap sheet is joined to the second core wrap sheet along a first stripe of juncture and a second stripe of juncture;

wherein the first stripe of juncture extends in a longitudinal direction;

wherein the second stripe of juncture extends a first distance in the longitudinal direction and a second distance in a transversal direction, and wherein the second distance is larger than the first distance; and wherein the first stripe of juncture or the second stripe of juncture comprises an adhesive and is nonlinear.

19. The absorbent article of claim 18, wherein the first stripe of juncture or the second stripe of juncture comprises an open area from about 30% to about 95% of the total area.

20. The absorbent article of claim 19, wherein the storage layer comprises a superabsorbent material, and wherein the superabsorbent material comprises at least 30% of the total weight of the storage layer.

21. The absorbent article of claim 18, wherein the first stripe of juncture or the second stripe of juncture is continuous.

22. The absorbent article of claim 18, wherein the first stripe of juncture or the second stripe of juncture is discontinuous.

23. The absorbent article of claim 18, wherein the first stripe of juncture or the second stripe of juncture comprises bonding elements.

24. An absorbent article having a longitudinal axis and a transverse axis, the absorbent article comprising:
 a topsheet;
 a backsheet; and
 an absorbent core disposed between the topsheet and the backsheet, the absorbent core defining a wearer facing side oriented towards a wearer when the absorbent article is being worn and an opposed garment facing side, wherein the core comprises: 1) a storage layer comprising a wearer facing side and an opposed garment facing side, 2) a first core wrap sheet covering the wearer facing side of the storage layer, and 3) a second core wrap sheet covering the garment facing side of the storage layer, wherein the first core wrap sheet is joined to the second core wrap sheet along a first stripe of juncture and a second stripe of juncture;

wherein the first stripe of juncture extends primarily in a longitudinal direction;

wherein the second stripe of juncture extends primarily in a transversal direction; and wherein the first stripe of juncture or the second stripe of juncture is curvilinear.

25. The absorbent article of claim 24, wherein the first stripe of juncture or the second stripe of juncture is continuous.

26. The absorbent article of claim 24, wherein the first stripe of juncture or the second stripe of juncture is discontinuous.

27. The absorbent article of claim 1, wherein the first stripe of juncture extends primarily in the longitudinal direction.

28. The absorbent article of claim 1, wherein the second stripe of juncture has a transversal length and a longitudinal width, and wherein the transversal length is greater than the longitudinal width.

29. The absorbent article of claim 18, wherein the first stripe of juncture extends a first distance in the longitudinal direction and a second distance in the transversal direction, and wherein the second distance is smaller than the first distance.

30. The absorbent article of claim 24, wherein the second stripe of juncture has a transversal length and a longitudinal width, and wherein the transversal length is greater than the longitudinal width.

* * * * *